United States Patent [19]

Dubrow et al.

[11] Patent Number: 5,227,205
[45] Date of Patent: Jul. 13, 1993

[54] SPECIMEN DISPLAY ARTICLE

[75] Inventors: Robert S. Dubrow, San Carlos, Calif.; Geoffrey Samuels, New York, N.Y.; Robert J. Molinari, Wayne, Pa.

[73] Assignee: Geoffrey Samuels, New York, N.Y.

[21] Appl. No.: 578,250

[22] Filed: Sep. 6, 1990

[51] Int. Cl.⁵ ............................................. A01N 3/00
[52] U.S. Cl. ....................................... 428/13; 156/57; 206/575
[58] Field of Search ................ 428/13, 15, 16, 17, 428/24; 427/4; 156/57; 206/223, 575

[56] References Cited

U.S. PATENT DOCUMENTS

| | | | |
|---|---|---|---|
| 748,284 | 12/1903 | Karwowski | 428/13 X |
| 2,567,929 | 9/1951 | Fessenden | 427/4 |
| 3,607,488 | 9/1971 | Yordan | 156/57 |
| 4,128,966 | 12/1978 | Spector | 428/13 X |
| 4,221,078 | 9/1980 | Latham et al. | 428/13 X |
| 4,272,571 | 6/1981 | Sierra et al. | 428/24 |
| 4,278,701 | 7/1981 | von Hagens | 427/4 |
| 4,320,157 | 3/1982 | von Hagens | 428/13 |
| 4,369,284 | 1/1983 | Chen | 524/476 |
| 4,600,261 | 7/1986 | Debbaut | 439/521 |
| 4,741,940 | 5/1988 | Reed | 428/68 |
| 4,777,063 | 10/1988 | Dubrow et al. | 427/44 |
| 4,864,725 | 9/1989 | Debbaut | 29/871 |
| 4,865,905 | 9/1989 | Uken | 428/220 |

Primary Examiner—Henry F. Epstein
Attorney, Agent, or Firm—Burns, Doane, Swecker & Mathis

[57] ABSTRACT

This invention provides improved means for displaying and preserving specimens of various kinds, such as flower blossoms. The medium for encapsulating the specimen is a resin material which, when fully cured, is soft and pliable, having a cone penetration value of about 80 to about 400 (10⁻¹mm) (ASTM D217-68 or D1403-69) and an ultimate elongation of at least about 100% (ASTM D638-80 or D412). This invention also provides a system for collecting specimens, preserving and dehydrating them, and transporting them to another site where the specimens are encapsulated in the soft, pliable resin for final preservation and display.

9 Claims, 1 Drawing Sheet

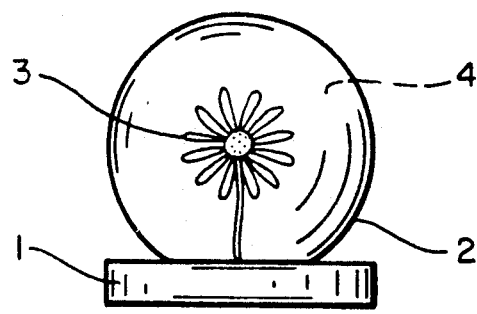
FIG_1
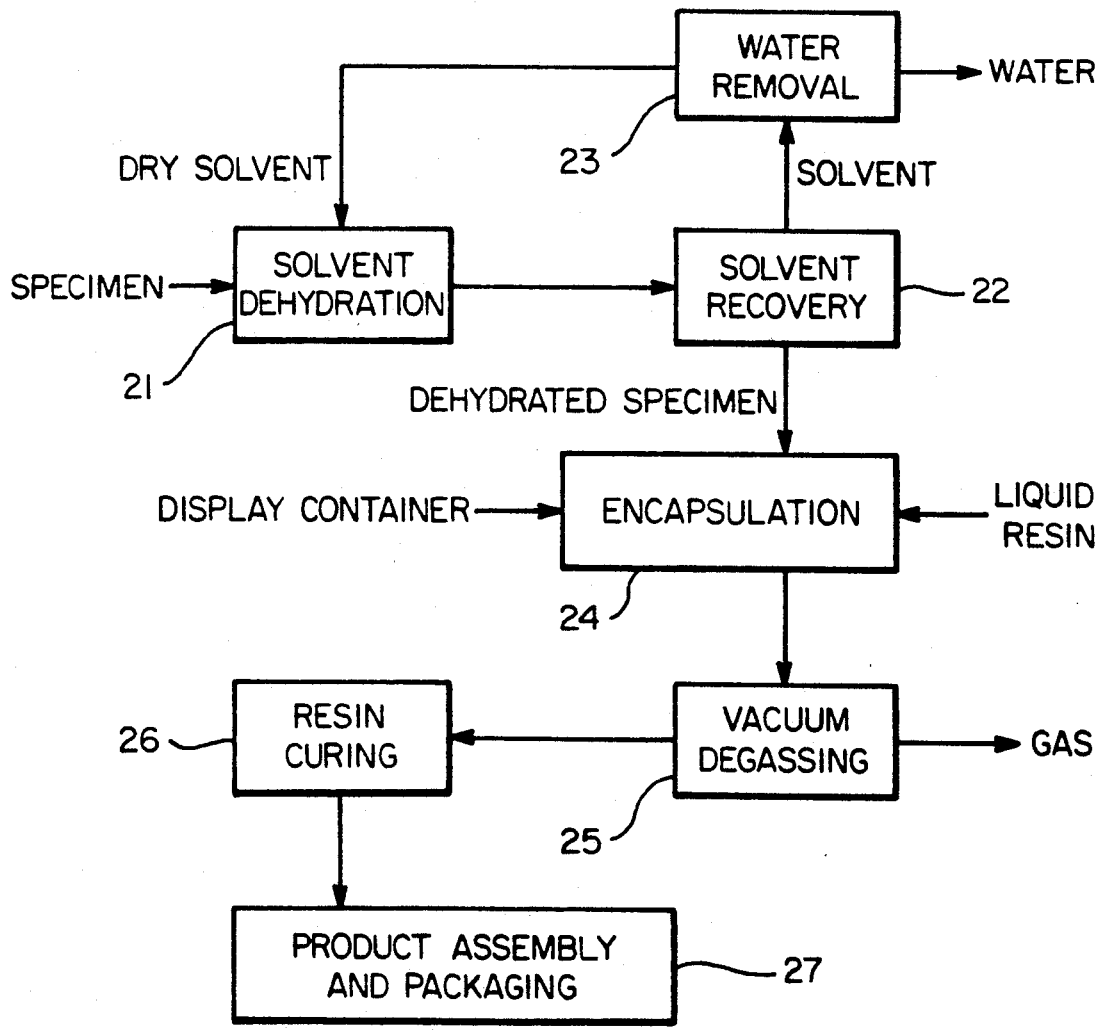
FIG_2

SPECIMEN DISPLAY ARTICLE

FIELD OF THE INVENTION

This invention relates to articles and methods for preserving and displaying specimens such as flowers.

BACKGROUND OF THE INVENTION

There has long been an interest in preserving and displaying specimens of various kinds. It is frequently desirable to preserve and display specimens for decorative purposes such as flower buds or blossoms, particularly those that have sentimental value such as from wedding bouquets and other special occasions. Other specimens which are desired for preservation and display are for scientific interests, education or medical training. Such specimens include plant or animal tissue including entire animals such as insects, butterflies, and spiders or particular portions or organs of animals.

Such specimens have been preserved and displayed in a variety of ways. One of the most common is simply the storage of the specimen in a preserving solution or liquid such as formaldehyde where the specimen and the liquid is contained in a glass or a transparent container for viewing. Similar decorative display arrangements for specimens include glass spheres which contain the specimen and water as the liquid containing the preservatives appropriate to prevent spoilage of the specimens in the water. Various disadvantages result from this type of preservation and display including the fact that the specimen may change shape or move in the liquid contained in the display container. The liquid medium also provides an opportunity for various components of the specimen to dissolve or diffuse into the liquid thereby contributing to the change in color or other properties of the specimen contained in the liquid.

Another way in which specimens have been preserved and displayed has been through the use of solid transparent resins such as acrylic resins whereby the specimen is dehydrated, then encapsulated in a clear resin, which is then cured to form a solid block. The block of resin then provides the means for preserving and displaying the specimen. Certain disadvantages have been encountered in this type of preserving and displaying specimens including the tendency for the hard, solid cured resin to crack or shrink or pull away from the specimen during the curing of the resin or after the resin has cured for an extended period of time. Hard resins such as the acrylics also tend to develop internal stresses upon curing which can either cause optical distortions or result in the cracking or shrinking which is undesired. Another disadvantage associated with this type of system for preserving and displaying specimens is the cost of preparing the display.

Another system for preserving and displaying specimens involves the dehydration of the specimen followed by impregnation of the specimen with a resin which preserves the specimen and also provides structural strength for the specimen after it is dehydrated. These systems also include the optional aspect of coating the specimen with the transparent resin to thereby enhance the preservation of the specimen as well as its strength and durability. These types of preserved specimens are also sometimes displayed in glass or transparent display case or removable bell jar or the like.

Various aspects of the above methods and systems for preserving and displaying various specimens are illustrated in U.S. Pat. No. 2,567,929 to Fessenden, U.S. Pat. No. 3,607,488 to Yordan, U.S. Pat. No. 4,272,571 to Romero-Sierra et al., and U.S. Pat. No. 4,278,701 to von Hagens. These disclosures are incorporated herein by reference.

It is an object of this invention to provide a more convenient and lower cost article, method and system for preserving and displaying various kinds of specimens. It is an object of this invention to overcome the disadvantages caused by the shrinking and cracking of the hard encapsulation resins as well as to eliminate the disadvantages encountered in preserving and displaying specimens in a liquid medium. These and other objects of this invention will become apparent from the disclosure herein.

SUMMARY OF THE INVENTION

In one aspect this invention comprises a specimen display article comprising a base for supporting a display container; a display container supported by the base and being transparent and adopted for holding and displaying a specimen; and a gel-type resin present in the display container in sufficient quantity to fill the container and encapsulate the specimen; wherein the gel-type resin is a cured solid which is soft, pliable and transparent.

In another aspect this invention comprises a method of preparing a specimen for display comprising dehydrating the specimen; placing the specimen and a liquid resin in a transparent display container to encapsulate the specimen in the liquid resin; and curing the resin to produce a solid gel-type resin which is soft, pliable and transparent.

In another aspect this invention comprises a kit of parts for encapsulating and displaying the specimen comprising a base for supporting a display container; a display container adapted to be supported by the base and being transparent and adapted for holding and displaying a specimen; and a liquid resin suitable for pouring into the display container in sufficient quantity to fill the display container and encapsulate a specimen present in the display container; wherein the resin is curable to a solid which is soft, pliable and transparent.

In another aspect this invention comprises a system for preserving and displaying a perishable specimen in an encapsulation means comprising dehydration means for at least partial dehydration of the specimen at the site where the specimen exits in fresh form; means for transporting the dehydration means to a separate location where the encapsulation means exists; means for removing the specimen from the dehydration means; means for positioning the specimen in a display container adapted for containing a liquid resin and for containing the resin in cured form; encapsulation means for adding liquid resin to the display container to encapsulate the specimen therein; means for curing the liquid resin to provide a cured solid polymer having a cone penetration of about 80 to about 400 ($10^{-1}$ mm) and an ultimate elongation of at least about 100%; and means for transporting the dehydration means back to the specimen site for collection of an additional specimen.

In each of the above aspects, it is preferred to include a degassing step, usually by applying a vacuum, to remove visible gas bubbles in the liquid resin and from around the specimen before curing the resin.

BRIEF DESCRIPTION OF THE DRAWING

FIG. 1 illustrates an article according to a preferred embodiment of this invention.

FIG. 2 illustrates a system for collecting, preserving and displaying specimens according to this invention.

DESCRIPTION OF THE INVENTION

This invention provides articles, methods and systems for preserving and displaying various specimens in various ways and for a variety of purposes. Of particular interest in the utility of the present invention is the preservation and display of fresh flowers and other decorative items, particularly those of sentimental value such as flower blossoms from wedding bouquets and the like. However, the present invention has equal utility for scientific and educational purposes for preserving and displaying various animal, plant or mineral specimens for an appropriate educational or scientific purpose. Likewise, this invention is useful for preserving and displaying specimens for novelty purposes.

As mentioned above, various problems have been encountered in the methods used to preserve and display specimens. The present invention provides an improved and superior method and system for producing specimens preserved and displayed in desired articles. The present invention also provides this improved result at lower cost than has been encountered with many of the solid resin encapsulation or encasement systems.

The present invention provides a unique medium for preserving and displaying a specimen in a transparent display container. The encapsulation medium employed in the present invention is neither liquid nor a hard solid. The material or medium used in this invention which provides many of the advantages provided by this invention is a material which has unique properties. The medium or material used in this invention is obtained by curing or polymerizing a liquid resin to produce a cured and stable resin which is a very soft, pliable and highly elastic material. The resin before and after curing is substantially transparent as desired for the particular application.

In its fully cured and stable form, the resins used in this invention are referred to as gel-type resins. In their cured form, they are very soft. In fact, the materials are so much softer than conventional elastomers that the hardness or softness of the materials cannot be measured on standard hardness scales used for elastomers and rubber-type polymers. The materials used in this invention can have a hardness or softness equivalent to a grease, such as petroleum jelly. Consequently, the hardness or softness of these materials is measured by a standardized cone penetration test, ASTM No. D217-68 or ASTM No. D1403-69. In particular, it is preferred that the materials used in this invention in their cured and stable form will have a cone penetration value in the range of about 80 to about 400 ($10^{-1}$ mm), preferably these materials have a cone penetration value of at least about 100, preferably from about 150 to about 300 and, most preferably, between about 175 and about 275.

In addition to being unusually soft, the gel-type resins useful in this invention also have a high degree of elongation or elasticity. In other words, these resins in their cured form can be elongated at least 100% without breaking and can return to their original shape and configuration without any distortion or tearing. The elongation property of these materials is generally recognized as measured in terms of the ultimate elongation, i.e., percent elongation to failure or tearing of the resin is measured by ASTM No. D638-80 or ASTM No. D412. In particular, it is generally preferred that these gel-type resins in their cured form will have ultimate elongation of at least about 100%, more preferably, at least about 200%. However, many of the gel-type resins useful in the present invention will have ultimate elongation properties of 300%, 500%, 800% or higher. In addition, many of the gel-type resins useful in the present invention have in their cured and stable state a high surface tack characteristic. This characteristic exhibits itself whether the liquid resin is cured in contact with a surface, such as the specimen or the display container or is cured not in contact with a surface. In either case, the gel-type resins in their cured state exhibit a high surface tack which is advantageous in the practice of this invention. It is preferred to contact the liquid resin with the specimen and cure the resin in contact with the surface of the specimen. In this way the surface of the specimen is best protected from the environment by the soft and pliable cured solid resin. And, due to the elongation properties and surface tack of the cured resin, the resin will remain in good contact with the surface of the specimen, even though slight movement, such as expansion/contraction occurring in heating/cooling temperature change cycles. Tensile strength is not particularly important for the cured resin; it need only have sufficient tensile strength to enable it to have the desired percent elongation properties mentioned above.

The above properties of the gel-type resins used in the present invention combine and cooperate to provide various advantages flowing from the present invention. The liquid uncured resin has a low viscosity so that, when it is used to encapsulate the specimen or the specimen is immersed in the liquid resin before it is cured, good contact between the specimen and the liquid resin and between the display container and the liquid resin is achieved. As explained herein, the liquid resin should have sufficiently low viscosity so that it is practical to degas the specimen and the liquid resin when desired before curing the resin. However, after the resin has cured the above described cone penetration and elongation properties, as well as the surface tack properties, provide the following advantages. As the resin cures the resin will not crack or pull away from the specimen or the display container surface. Moreover, the resin is sufficiently resilient and flexible such that it will not separate from the specimen or the display container surfaces nor will it crack on changes of temperature or upon the specimen changing shape or deforming slightly after the resin is cured. The cured gel-type resin also acts as a very effective encapsulant and sealant for the specimen thereby preventing moisture or humidity from reentering the specimen after it has been dehydrated in preparation for encapsulation and display. Similarly, the resin prevents further dehydration or changes in the specimen. However, despite the extreme softness of the gel-type resins used in the present invention the resin is nevertheless sufficiently strong and has sufficient resilience to maintain the specimen substantially in the desired position and in its original shape. Thus, even if the specimen should tend to deform in shape the gel-type resin used in this invention would maintain its original shape. Nevertheless, any slight movement of the specimen will not affect the effectiveness of the encapsulation thereof by the system of this invention because the elasticity and surface tack of the cured resin enables it to maintain a sealed relationship to the surface of the specimen. The high degree of effectiveness of the sealing and encapsulation of the specimen against moisture and other environmental conditions also helps prevent the specimen from tending to change shape after it has been immersed in the resin and the resin cured to form the soft and pliable encapsulation system of this invention.

Gel-type resins are known in the art for other uses and various types of chemical resin systems can be used in the present invention. The resin system preferred for use in the present invention are the curable organopolysiloxane materials, which are preferred because of their optical clarity, ease of cure and stability and inertness in the cured form. However, other resin systems such a polyurethanes, styrene-ethylene-butadyene-styrene copolymers, and the like may be used. An exemplary disclosure of the polysiloxane gel-type polymers appears in U.S. Pat. No. 4,777,063 to Dubrow et al., polyurethane gel-type polymers are discussed in U.S. Pat. Nos. 4,600,261 and 4,864,725 to Debbaut, and in U.S. Pat. No. 4,865,905 to Uken, and SEBS-type block copolymer gel-type resins are exemplified by U.S. Pat. No. 4,369,284 to Chen. The selection of the particular polymer having the desired physical properties of cone penetration and ultimate elongation as discussed above for use in this invention will be clear to one skilled in the art depending on the other properties desired in the liquid and the cured gel-type resin. For example, color or optical quality, UV stability, high temperature or low temperature stability, etc., will all be factors to be considered in the selection of the gel-type resin for use in this invention. In addition, other factors such as compatibility with the specimen to be preserved and displayed, speed of cure, room temperature versus elevated temperature, etc., will also be factors to be considered by one schooled in the art in utilizing the present invention. One skilled in the art will also recognize that the appropriate curing catalyst system will need to be selected to provide full curing of the gel-type resin compatible with the nature of the specimen and the curing conditions selected for use in this invention.

The organopolysiloxane resins are preferred in most embodiments of the present invention due to their optical clarity as well as other properties including compatibility with most materials and specimens, lack of toxicity, speed of cure, etc. An appropriate polysiloxane liquid which is curable to provide the desired cone penetration and elongation properties mentioned above can be selected from those commercially available including the "Dow 200" and the "Dow 527" systems available from Dow-Corning, KE104 available from Shin-Etau, PS426, available from Petrarch, and the like. The various polysiloxane systems are formulated so that when they fully cure and the cross linking is completed they have the desired cone penetration and ultimate elongated properties as discussed herein.

The specimens for which the present invention is applicable includes any variety of animal, plant and mineral specimens. The animal type specimens will include entire animals such as insects, spiders, reptiles, mammals, etc. as well as animal tissue specimens including entire organs. The plant-type specimens can likewise include entire plants or portions thereof including sections and plant tissue specimens, leaf specimens and of particular interest for this invention are the flower, bud and blossom specimens. The mineral type specimens can include rocks, crystals, powders and the like.

The display container useful in this invention will generally be a transparent glass or polymeric type container which is compatible with the specimen and the gel-type resin used in the container. The optical clarity and/or color of the display container will depend upon the particular display desired. The display container will normally be supported by a base which may be a separate member or an integral of the display container itself depending on the type of display desired for the article as a whole.

As used herein, "transparent" is intended to include any degree of optical clarity or translucent quality which provides the desired display and effect for the specimen included in the article and method of this invention. In other words, if the specimen is to be clearly displayed, then the display container and gel-type resin should optically clear, but in those instances where a desired special effect is to be imparted by a translucent or partially translucent display container, with either a clear or an additionally translucent or colored gel-type resin, for purposes of the present invention, all such degrees of clarity or translucent qualities in the display container and the gel-type resin are included within the scope of "transparent" for purposes of the present invention provided that the desired degree and quality of visibility of the displayed specimen is available in the final article.

The dehydration step which is performed on many specimens whether they are animal tissue or plant tissue or mineral specimens can be carried in conventional ways as discussed and disclosed in the background references mentioned above. The conventional dehydration techniques include solvent dehydration, oven dehydration and vacuum dehydration.

The degassing step is a preferred and optional, but generally important, step which is to be performed after the specimen is placed in the liquid resin and before the resin is cured. The degassing is generally performed by subjecting the display container having the specimen and liquid resin therein to a vacuum in order to remove and display the gas bubbles which may be present in the specimen or the liquid resin. After the degassing step is completed, then the resin is cured to prevent gas from reentering the specimen or the resin. The amount of vacuum which is applied to perform the degassing step is conventional and apparent to one skilled in the art and will depend on the specimen present as well as the volatility of the liquid resin as well as other factors present. Another preferred method is the use of a vacuum oven to simultaneously degas and cure the resin in the system. The use of the vacuum oven enables removal of gas at elevated temperatures where it expands and is easier to remove before the resin is cured.

The drawings illustrate particular embodiments of this invention. In FIG. 1, transparent glass dome 2 is supported by base 1. Flower specimen 3 that has been dehydrated previously is encapsulated in and supported by a gel-type polymer 4. The polymer is a transparent polysiloxane which has a cone penetration value of about 260 ($10^{-1}$ mm) and an ultimate elongation of about 400 to 600% when fully cured. The article of FIG. 1 is made by inverting the glass dome, suspending the dehydrated flower in the desired position with a temporary support and filling the glass dome with polysiloxane fluid polymer through the opening in the bottom of the glass dome. After vacuum degassing, the polymer is cured in an oven at elevated temperature. After the polymer is cured, the temporary support is removed and the base affixed to the bottom of the glass dome to cover the opening therein and provide means for displaying the dome and specimen in the upright position.

FIG. 2 illustrates an example of the system of this invention wherein the dehydration is by solvent dehydration. A selected specimen such as a flower, is placed in a container of solvent in a dehydration step 21. After a suitable period of time the solvent is recovered in step 22, and the recovered solvent is subjected to water removal step 23 and the dry solvent recycled for use again in step 21. The dehydrated specimen is encapsulated in step 24 by positioning in a display container and adding the liquid resin. After vacuum degassing in step 25 and resin curing in step 26, the final display article is assembled and packaged for shipment in step 27.

An important aspect of this system is the use of a gel-type resin, which provides the various advantages discussed herein. Another important aspect of this system is that it enables specimens to be obtained, dehydrated and preserved in step 21 at a location remote from where the encapsulation and resin curing steps 22, 23, 24, 25, 26 and related operations are performed. This particularly enables the use of this system in an ongoing operation. For example, flower specimens obtained by a florist from special occasion bouquets, such as wedding arrangements, can be preserved in step 21 and shipped to a central location where steps 22-27 are performed. The final product containing the preserved flower in the display article is then returned to the florist for presentation to the customer. Fresh, dry solvent is also again supplied to the florist for further use. Similar remote-central operations are enabled for other purposes, such as field collection of specimens of plant, animal, or mineral samples. Other applications of this system will be apparent to one skilled in the art.

Having described the invention in general and preferred terms, the following examples are now included to set forth specific embodiments of the present invention.

EXAMPLE 1—FLOWER DEHYDRATION

Four flowers were dehydrated, a red rose, pink rose, pink carnation and yellow daisy. Each flower was fresh and stored with the stem in water before cutting. When the flowers were cut, two inches of stem was left intact with the flower.

The flowers were mounted onto a holder consisting of a steel bar approximately 0.5×4.0×0.25" which had a strand of piano wire attached to it so that the rose was suspended perpendicularly from the bar about two inches from the bar. Each cut flower was mounted onto a base by forcing the piano wire into the stem.

Dehydration solutions were prepared using the following formulation:

| | |
|---|---|
| Tertiary Butyl Alcohol | 450 grams |
| Isopropanol | 50 grams |
| Citric Acid | 5 grams |
| Thiourea | 10 grams |

The flowers were lowered into the preserving solution so that they were completely immersed. They were allowed to soak for about 20 hours at 25° C. The dehydrated flower was then taken out and placed into a desiccating oven at 60° C. for about two hours, then in a desiccator until potting.

All flowers maintained essentially their original shape and coloring.

EXAMPLE 2—ENCAPSULATION

A low viscosity curing resin was prepared for potting the flowers. It was composed of the following ingredients.

| | |
|---|---|
| McGann NuSil 5602 | 15 pts |
| Dow Corning 200 Fluid | 85 pts |
| McGann NuSil 5602 Curing Agent | 0.5 pts |

The ingredients were mixed well and then degassed under a vacuum of 28 mm of Hg. The compound was water clear. The mixture was then transferred to a clear glass dome with a four inch diameter. The dome was filled to within one centimeter of the rim of the opening which required about 450 grams of material.

A flower from Example 1 was then removed from the desiccater and placed upside down into the dome. The steel base was left on the flower and served as a weight to hold the light flower in place in the resin. The dome was then placed into a vacuum oven and degassed for 15 minutes at 28 mm of Hg. After degassing, the resin was allowed to cure to its gel-type properties by heating it for 24 hours at 60° C.

The resin cured to a water clear gel while leaving the flower undamaged and not altering its color. There was no evidence of the resin pulling away from the dome during curing.

EXAMPLE 3

The above procedures of Examples 1 and 2 were repeated using a spider as the specimen instead of a flower. The spider was dehydrated for two hours and the resin was cured for 6 hours at 40° C. A similar result was observed.

Having described this invention in general and specific terms to enable one skilled in the art to practice this invention, the scope of the invention is to be determined by the appended claims.

What is claimed is:

1. A specimen display article comprising:
   a base for supporting a display container;
   a display container supported by the base and being transparent and adapted for holding and displaying a specimen;
   and a gel-type resin present in the display container in sufficient quantity to fill the container and encapsulate the specimen;
   wherein the gel-type resin is a cured solid which is soft, pliable and transparent.

2. An article according to claim 1 wherein the resin is a polysiloxane cured to have a cone penetration value of about 80 to about 400 ($10^{-1}$ mm).

3. An article according to claim 1 wherein the resin has an ultimate elongation of at least about 100%.

4. An article according to claim 1 wherein the specimen comprises plant tissue.

5. An article according to claim 1 wherein the specimen comprises a flower bud or blossom.

6. An article according to claim 2 wherein the specimen comprises a flower bud or blossom.

7. An article according to claim 1 wherein the specimen comprises animal tissue.

8. An article according to claim 1 wherein the display container comprises a glass sphere.

9. A kit of parts for encapsulating and displaying a specimen comprising:

a base for supporting a display container;

a display container adapted to be supported by the base and being transparent and adapted for holding and displaying a specimen; and a gel-type resin suitable for pouring into the display container in sufficient quantity to fill the display container and encapsulate a specimen present in the display container;

wherein the resin is curable to a solid which is soft, pliable and transparent.

* * * * *